United States Patent [19]
Goralski et al.

[11] 3,948,948

[45] Apr. 6, 1976

[54] 3,4-DIHALO-2,5-THIOPHENEDICARBONI-TRILES

[75] Inventors: Christian T. Goralski; R. Garth Pews, both of Midland; George A. Burk, Bay City, all of Mich.

[73] Assignee: The Dow Chemical Company, Midland, Mich.

[22] Filed: Nov. 23, 1973

[21] Appl. No.: 418,536

[52] U.S. Cl............................. 260/332.5; 424/275
[51] Int. Cl.² ........................................ C07D 333/12
[58] Field of Search.................... 260/332.5; 71/105; 424/275

[56] References Cited
UNITED STATES PATENTS

| | | | |
|---|---|---|---|
| 2,551,572 | 5/1951 | Denton et al. | 260/329 |
| 2,809,983 | 10/1957 | Heininger | 71/105 |
| 3,272,795 | 9/1966 | Heywood et al. | 71/105 |
| 3,278,553 | 10/1966 | Weil | 260/332.5 |
| 3,290,353 | 12/1966 | Battershell et al. | 71/105 |
| 3,526,497 | 9/1970 | Obreiter | 71/105 |
| 3,726,662 | 4/1973 | Howe et al. | 71/105 |
| 3,865,866 | 2/1975 | Ozaki et al. | 71/105 |

OTHER PUBLICATIONS

Burger, "Medicinal Chemistry," Part I, (3rd Ed.), (1970), pp. 72, 73.
Rappoport, "The Chemistry of the Cyano Group," (1970), p. 92.

*Primary Examiner*—James O. Thomas, Jr.
*Assistant Examiner*—A. Siegel
*Attorney, Agent, or Firm*—Theodore Post; C. Kenneth Bjork

[57] ABSTRACT

3,4-Dihalo-2,5-thiophenedicarbonitriles of the formula

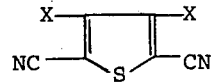

wherein each X independently is chloro or bromo. The compounds have plant fungicidal activity.

3 Claims, No Drawings

3,4-DIHALO-2,5-THIOPHENEDICARBONITRILES

BACKGROUND OF THE INVENTION 2,3-, 2,4-, 2,5- and 3,4-Thiophenedicarbonitriles are known; Bull. Soc. Chim. France 1969: 2511. No utility is taught for any for these compounds.

SUMMARY OF THE INVENTION

This invention concerns 3,4-dihalo-2,5-thiophenedicarbonitriles corresponding to the formula

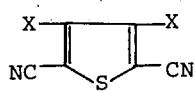

wherein each X independently represents chloro or bromo. The compounds have plant fungicidal activity.

DESCRIPTION OF THE PREFERRED EMBODIMENTS

The compounds are prepared by heating a solution of a corresponding 3,4-dihalo-2,5-thiophenedicarboxime in acetic anhydride at an elevated temperature of about 130°C. for about one hour to remove the elements of water according to the following equation

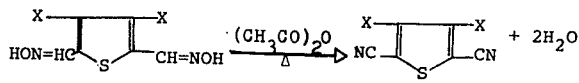

From about 20 to about 30 moles of acetic anhydride per mole of the dicarboxime are advantageously used. The reaction mixture is then poured into ice water and the precipitated product is recovered and recrystallized from methanol.

The following additional description and examples further describe the invention and the manner and process of making and using it to enable the art skilled to make and use the same and set forth the best mode contemplated by the inventors of carrying out the invention.

Preparation A:

3,4-Dibromo-2,5-thiophenedicarboxime intermediate

A solution of 10 g. (0.25 mole) of sodium hydroxide in 100 ml. of water is mixed with one containing 12.5 g. (0.18 mole) of hydroxylamine hydrochloride in 150 ml. of water, and the resulting solution added to a rapidly stirring slurry of 15 g. (0.05 mole) of 3,4-dibromo-2,5-thiophenedicarboxaldehyde in 100 ml. of water. After digesting on a steam bath for 1 hour, the reaction mixture is stirred into 400 ml. of aqueous 2% hydrochloric acid. The precipitated solid is recrystallized from ethanol to give 15 g. (91% yield) of the title compound, m.p. 225°C. Anal. Calcd. for $C_6H_4Br_2N_2O_2S$: C, 22.00; H, 1.22; Br, 48.60; N, 8.50; S, 9.70.

Found: C, 21.76; H, 1.44; Br, 47.70; N, 8.21; S, 9.60.

EXAMPLE 1:

3,4-Dibromo-2,5-thiophenedicarbonitrile

A solution of 8.0 g. (0.024 mole) of 3,4-dibromo-2,5-thiophenedicarboxime in 60 ml. of acetic anhydride is heated at reflux temperature, ca. 130°C. until reaction substantially ceases (for ca. 1 hour) then cooled to substantially room temperature. The cooled reaction mixture is poured into ice water, and the precipitated solid is recrystallized from methanol to give 5.40 g. (76% yield) of the title compound as a yellow solid, m.p. 138°-139°C. Anal. Calcd. for $C_6Br_2N_2S$: C, 24.70; N, 9.50; S, 11.00.

Found: C, 25.10; N, 9.58; S, 10.70

Preparation B:

3,4-Dichloro-2,5-thiophenedicarboxime intermediate

A solution of 4.0 g. (0.1 mole) of sodium hydroxide in 40 ml. of water is mixed with one containing 5.0 g. (0.072 mole) of hydroxylamine hydrochloride in 60 ml. of water, and to the resulting solution 4.2 g. (0.02 mole) of 3,4-dichloro-2,5-thiophenedicarboxaldehyde containing a minor proportion of mixed 3,4-bromochloro-2,5-thiophenedicarboxaldehyde, is added. The reaction mixture is heated on a steam bath for 20 minutes, then allowed to cool. The crude product is filtered off and recrystallized from ethanol to give 2.40 g. (50% yield), of product which is predominantly the title compound having a minor proportion of mixed 3,4-bromochloro product, m.p. 228°C. Anal. Calcd. for $C_6H_4Cl_2N_2O_2S$: C, 30.14; H, 1.68; N, 11.72; S, 13.41.

Found: C, 26.5; H, 1.60; N, 9.70; S, 12.80.

The corresponding 3-bromo (or chloro)-4-chloro (or bromo)-2,5-thiophenedicarboxime is similarly prepared.

EXAMPLE 2:

3,4-Dichloro-2,5-thiophenedicarbonitrile

A solution of 1.5 g. of 3,4-dichloro-2,5-thiophenedicarboxime in 10 ml. of acetic anhydride is heated at reflux for ca. 2 hours until reaction ceases. The reaction mixture is allowed to cool to substantially room temperature, then is poured into ice water, yielding a yellow solid. The solid is filtered off and recrystallized from methanol to give 0.94 g. (74% yield) of product, m.p. 128°C. Elemental analysis shows 22.9% chlorine and 19.2% bromine, equivalent to 1.5 atom of chlorine and 0.5 atom of bromine per molecule.

The corresponding 3-bromo (or chloro)-4-chloro (or bromo)-2,5-thiophenedicarbonitriles are similarly prepared.

The products of the invention have plant antifungal activity. This is not to suggest that the compounds of the invention and mixtures thereof with usual additives are equally effective against such fungi at the same concentration. For such uses the compounds can be employed in an unmodified form or dispersed on a finely divided solid and employed as a dust. Such mixtures can also be dispersed in water with the aid of a surface-active agent and the resulting emulsion employed as a spray. In other procedures, the products can be employed as the active constituents in solvent solutions, oil-in-water or water-in-oil emulsions. The augmented compositions are adapted to be formulated as concentrates and subsequently diluted with additional liquid or solid adjuvant to produce the ultimate treating compositions. Good results are obtained when employing compositions containing plant antifungal concentrations and usually from about 100 to about 5000 parts by weight of one or more of the compounds per million parts of such compositions.

In representative operations, the compounds of Examples 1 and 2 when tested for fungicidal activity using a conventional post-emergent application test gave 95% to 100% control of bean mildew at a 100 to 4000 p.p.m. concentration. In a conventional agar dilution test, both compounds gave 50% growth inhibition of T. mentagrophytes at a concentration of 100 parts per million by weight. The analogous mixed 3-bromo (or chloro)-4-chloro (or bromo)-2,5-thiophene dicarbonitriles have similar activity, as would be expected.

The starting materials for the intermediates, i.e., for the corresponding 3,4-dihalo-2,5-thiophenedicarboxaldehydes, and for their starting materials, i.e., the corresponding 3,4-dihalo-2,5-bis(dibromomethyl)thiophenes are prepared by procedures disclosed by Steinkopf e.a., Ann. 532, 250 (1937).

What is claimed is:

1. A compound corresponding to the formula

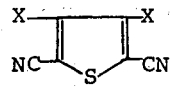

wherein each X individually represents chloro or bromo.

2. The compound of claim 1 which is 3,4-dibromo-2,5-thiophenedicarbonitrile.

3. The compound of claim 1 which is 3,4-dichloro-2,5-thiophenedicarbonitrile.

* * * * *